United States Patent [19]
Alive et al.

[11] Patent Number: 5,811,599
[45] Date of Patent: Sep. 22, 1998

[54] PROCESS FOR THE SELECTIVE OXIDATION OF HYDROCARBONS AND THEIR DERIVATIVES

[76] Inventors: Keshavaraja Alive; Ramaswamy Arumugamangalam Venkataraman; Ratnasamy Paul, all of National Chemical Laboratory, Pune-411008, Maharashtra, India

[21] Appl. No.: 510,291

[22] Filed: Aug. 2, 1995

[30] Foreign Application Priority Data

Dec. 30, 1994 [IN] India ............................. 1722/Del/94

[51] Int. Cl.$^6$ ...................................... C07C 37/00
[52] U.S. Cl. ..................... 568/771; 568/719; 568/741; 568/780; 568/803; 568/836; 549/518
[58] Field of Search .................... 568/719, 741, 568/780, 771, 803, 836; 549/518

[56] References Cited

PUBLICATIONS

Ratnasamy, P. and A.J. Leonard. "X–Ray Scattering Techniques in the Study of Amorphous Catalysts" *Catalysis Reviews* 6(2): 293–322 (1972).

Romano, et al. "Selective oxidation with Ti–silicalite" *La Chimica & L'Industria* 72: 610–616 (1990).

Kooyman, et al. "Titanium deposited from TiCl$_4$ on amorphous silica and silicalite–1 as catalyst in aromatic hydroxylation reactions" *Catalysis Letters* 13: 229–238 (1992).

*Primary Examiner*—Samuel Barts
*Attorney, Agent, or Firm*—Foley, Hoag & Eliot LLP

[57] ABSTRACT

A process for the oxidation of hydrocarbons and their derivatives having the general formula RX, wherein R is from n-alkyl, iso-alkyl, benzyl, cyclohexyl, mono, di or tricyclic aryl, or alkenic groups and X is selected from H, OH or Cl to compounds having formula R$^1$XY wherein R$^1$=(R—H), X has the meaning defined as above and Y=OH; which comprises of reacting the appropriate hydrocarbon or it's derivative of the formula RX where R and X have the meaning given above, with a solution of aqueous hydrogen peroxide at a temperature in the range of 10°–100° C. in the presence of an amorphous titanium-silicate catalyst having molar chemical composition in terms of the anhydrous oxides of TiO$_2$: (5-400) SiO$_2$, having an average micropore radius between 10 and 40 Å, an absorption band around 220 nm in the ultraviolet region, a band around 960 cm$^{-1}$ in the infrared region, interatomic vectors around 1.6–1.7, 2.7–2.8, 4.1–4.2 and 5.0–5.2 Å in the radial electron density distribution and absence of any line in the x-ray diffraction pattern; and isolating the resultant products of the oxidation reaction by conventional methods.

8 Claims, 2 Drawing Sheets

PROCESS FOR THE SELECTIVE OXIDATION OF HYDROCARBONS AND THEIR DERIVATIVES

BACKGROUND OF THE INVENTION

1. Field of the Invention

This invention relates to a process for the selective oxidation of hydrocarbons and their derivatives. More particularly, this invention deals with the selective oxidation of hydrocarbons and their derivatives using hydrogen peroxide as the oxidant in the presence of an amorphous titanium-silicate catalyst.

The process of the present invention can be advantageously used particularly in the selective oxidation in general and more particularly in the following reactions:
1. Conversion of Benzene to Phenol
2. Conversion of Toluene to cresols
3. Conversion of Xylene to xylenols
4. Conversion of Napthalene to napthols
5. Conversion of Anthracene to hydroxy anthracenes
6. Conversion of n-alkanes to n-alkanols
7. Conversion of Cyclohexane to cyclohexanol
8. Conversion of Propylene to propylene oxide
9. Conversion of Styrene to styrene oxide
10. Conversion of Phenol to hydroquinone and catechol
11. Conversion of Allyl alcohol to glycidol

2. Description of the Prior Art

In the prior art, titanium on amorphous titanium-silica catalysts are known to catalyse epoxidation of olefins and hydroxylation of aromatics like phenol, using organic hydro-peroxides as the oxidising agents. For example, GB Patent 1, 249, 079 to Shell Oil describes the use of a titanium-on-amorphous silica as a catalyst to epoxidise propylene to propylene oxide, the said catalyst being obtained by the reaction of a compound of titanium with solid silica of high surface area, followed by transformation of the titanium compound into the oxide, using organic hydroperoxides such as tertiary butyl hydroperoxide or ethylbenzene hydroperoxide as the oxidising agents. One drawback of prior art processes of hydrocarbon oxidation using titanium-amorphous silica catalysts is that they possess high activity and selectivity in the oxidation process only when organic hydroperoxides are used as oxidising agents. When other more convenient oxidising agents like hydrogen peroxide are used the activity and selectivity are lower. One drawback of oxidising agents like organic hydroperoxides is the production of stoichiometric quantities of byproducts. For example, in the oxidation of propylene to propylene oxide using organic hydroperoxides, for every ton of propylene oxide, 2.5 tons of methylphenylcarbinol or 3 tons of tertiary butyl alcohol are coproduced whose disposal poses special problems. When $H_2O_2$ is used as the oxidising agent, water is the only coproduct which can be eleminated easily, if necessary.

Attempts have been made in the prior art to develop hydrocarbon oxidation processes with titanium-on-amorphous silica catalysts using $H_2O_2$ as oxidising agent. Use of $TiCl_4$ in an organic solvent for the deposition of Ti in amorphous silica had been employed by a number of workers. P. J. Kooyman et al [Catalysis Letters, Vol. 13 (1992), p. 229–238] used this method to deposit Ti on a pentasil type silicalite and studied the oxidation of phenol using $H_2O_2$ as an oxidising agent but found only a low selectivity (30–40 mole %) towards the hydroxylation products.

Crystalline titanium silicalite molecular sieves (TS-1) synthesised hydrothermally are able to overcome this drawback of titanium-on-amorphous silica and catalyse the oxidation of hydrocarbons using $H_2O_2$ as oxidising agent with high activity and selectivity. U.S. Pat. No. 4,410,501, GB 2, 116, 974 and the report of U. Romano et al. in La Chimica and L'Industria, Vol. 72 (1 990) p. 610 describe the preparation and applications of TS-1 in selective oxidation processes.

One drawback of TS-1 and, in fact, of most crystalline molecular sieve-based catalysts is that while they are highly active and selective in catalytic reactions involving small molecules, they are inactive when the dimensions of the reactant molecules are larger than the pore size of the molecular sieve thereby excluding the reactants from access to the internal pores of the molecular sieve wherein practically all the active sites needed for the catalytic conversion are located (See Table 1 below).

TABLE 1

Feasibility of carrying out activation of some organic substrates.

| | Catalyst | |
|---|---|---|
| Molecules | TS1 | MMATS |
| Benzene | yes | yes |
| phenol | yes | yes |
| napthalene | no | yes |
| 1 napthol | no | yes |
| anthracene | no | yes |

Thus, while TS-1 is highly active in the conversation of benzene to phenol and phenol to a mixture of dihydroxy benzenes, it is totally inactive in the oxidation of napthalene to napthols and napthols to dihydroxy napthalenes (Please refer Table 2 shown below).

TABLE 2

A comparison of activities of TS-1 and MMATS in the hydroxylation of differenct organic substrates.

| | Conversion (wt %) | |
|---|---|---|
| Molecules | TS1 | MMATS |
| Benzene | 40 | 52 |
| phenol | 88 | 90 |
| napthalene | nil | 68 |
| 2 napthol | nil | 45 |

Many of the oxidation processes in the fine chemicals industry involve the selective oxidation of bulky hydrocarbons or their derivatives. It would be desirable to use an environmentally clean oxidising agent like $H_2O_2$ in such processes.

It is particularly noteworthy that the prior art teaches that both the utilisation of nitrogenated organic bases during preparation and the presence of a long range crystalline order, as in TS-1, are essential features of any titanium-silicate catalyst used in the selective oxidation processes utilising $H_2O_2$ as the oxidising agent. It has been observed that certain amorphous titanium-silicates prepared in the absence of any nitrogenated organic phase and especially those devoid of any crystalline structure are effective in the selective oxidation of hydrocarbons or their derivatives using $H_2O_2$ as the oxidising agent.

SUMMARY OF THE INVENTION

It is an object of the present invention to provide an improved process for the oxidation of hydrocarbons or their derivatives using $H_2O_2$ as the oxidising agent and an amorphous titanium-silicate catalyst with an average micropore radius above 10 Å as the catalyst. Such a process would enable the selective oxidation of bulky hydrocarbons under environmentally clean conditions. Under the above said background the finding based on what the present has been developed is very surprising and unexpected.

DESCRIPTION OF THE PREFERRED EMBODIMENT

Figure 1:
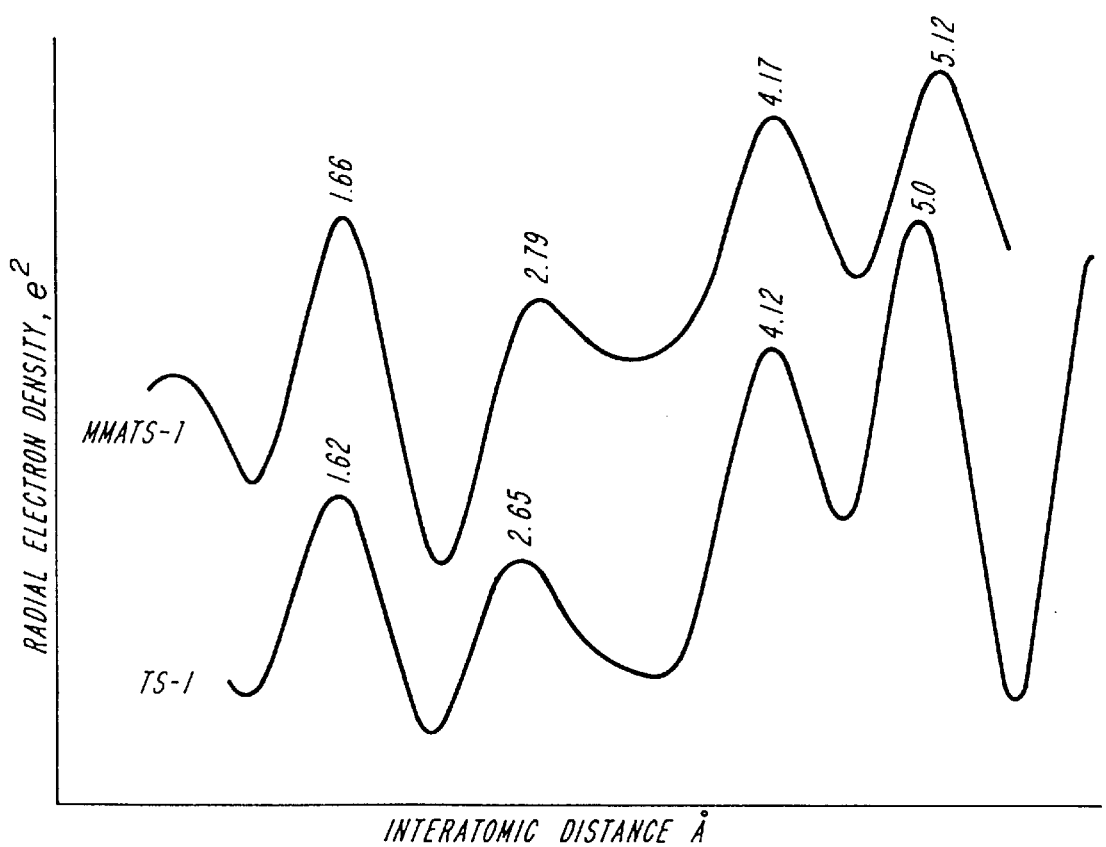
FIG. 1 illustrates the radial electron density of the material of the present invention.

Accordingly, the present invention provides a process for the oxidation of hydrocarbons and their derivatives having a general formula RX, wherein R is from n-alkyl such as methyl, ethyl, propyl, butyl and hexyl, isoalkyl such as isopropyl, benzyl, cyclohexyl, mono-, di- or tricyclic aryl such as benzene, napthalene and anthracene or alkenic groups and X is selected from H, OH or Cl to compounds having formula $R^1XY$ wherein $R^1$=(R—H, wherein R is from n-alkyl, isoalkyl, benzyl, cyclohexyl, mono-, di- or tricyclic aryl such as benzene, napthalene and anthracene or alkenic groups), X has the meaning defined as above and Y=OH, which comprises of reacting the appropriate hydrocarbon or it's derivative of the formula RX where R and X having the meaning defined above, with a solution of aqueous hydrogen peroxide at a temperature in the range of 10°–100° C., preferably between 50° to 100° C., in the presence of an amorphous titanium-silicate catalyst having molar chemical composition in terms of the anhydrous oxides of $TiO_2$: (5-400) $SiO_2$, having an average micropore radius between 10 and 40 Å, an absorption band around 220 nm in the ultraviolet region, a band around 960 $cm^{-1}$ in the infrared region and interatomic vectors around 1.6–1.7, 2.7–2.8, 4.1–4.2 and 5.0–5.2 Å in the radial electron density distribution and the absence of any line in the x-ray diffraction pattern; and isolating the resultant products of the oxidation reaction by conventional methods.

In one of the embodiments of the process of the present invention, selective oxidation of a hydrocarbon or its derivative with an aqueous solution of $H_2O_2$ is carried out under oxidation conditions in the presence of an amorphous titanium-silicate catalyst. Oxidation processes of the present invention include oxidation of hydrocarbons to hydroxy hydrocarbons, paraffinic hydrocarbons to alcohols and ketones and olefinic hydrocarbons to epoxides. The organic substrate that can be used is selected from benzene, toluene, xylene, napthalene, anthracene, n-alkanes, cyclohexane, propylene, styrene, phenol, allyl alcohol.

In another embodiment of the process of the present invention, the amorphous titanium-silicate catalyst is charaterised by the following distinctive features:

1. absence of any line in the x-ray diffraction pattern,
2. presence of a sharp absorption band around 220 nanometers in the ultraviolet region of the spectrum,
3. presence of a sharp absorption band around 960 $cm^{-1}$ in the infrared region of the absorption spectrum,
4. an average micropore radius below 10 Å and meso-pore radius below 40 Å;
5. a chemical composition, in terms of the mole ratios of the anhydrous oxides, of $TiO_2$: (5–400) $SiO_2$; and
6. the presence of interatomic vectors around 1.6–1.7, 2.7–2.8, 4.1–4.2 and 5.0–5.2 Å, in the radial electron density distribution.

Catalysts exhibiting the above six features have been used in the process described in the present invention for the selective oxidation of hydrocarbons using $H_2O_2$ as the oxidising agent.

While one or more of the six above mentioned features may be present in the prior art titanosilicates, the presence of all the six features is a unique and distinguishing characteristic of the material of the present invention. Thus, while prior art amorphous titanium silicates may possess the features 1,2 and sometimes even feature 5 mentioned hereinabove, they do not possess the remaining features, 3,4 and 6. Similarly, while prior art crystalline titanium silicates may exhibit features 1,3,4 and 6, they do not definitely possess features 2 and 5. To the applicants' knowledge, no single material is known in the prior art, which possesses simultaneously all of the above mentioned six features.

The synthetic material according to the present invention has characteristics which are demonstrated by standard techniques well know to those skilled in the art such as X-ray diffraction, IR spectroscopy, UV-Visible, X-ray Scattering and also catalytic test reactions. The chemical composition may be ascertained by conventional wet chemical methods. The absence of any line in the x-ray diffraction pattern, feature number 2, mentioned hereinabove, may be verified by a conventional powder diffractometer provided with an electronic pulse counting system.

Features 3 and 4 may be identified using conventional ultraviolet and infrared spectrometers, respectively. The bimodal pore size distribution, feature 5 may be evaluated from an absorption-desorption isotherm obtained using argon gas as the adsorbate in a conventional adsorption apparatus. The principles, apparatus and calculations involved in obtaining the interatomic vectors from the radial electron density distribution in amorphous materials is described in detail in chapter 12 of the text book titled "X-ray diffraction procedures for polycrystalline and amorphous materials" by H. P. Klug and L. E. Alexander, Second Edition 1974, published by Wiley Inc., N.Y. Further, additional information of particular relevance to the present invention is described in the review article titled "X-ray scattering techniques in the study of amorphous catalysts" by P. Ratnaswamy and A. J. Leonard in Catalysis Reviews, Vol. 6, p. 292 (1972) published by Marcel Dekker Inc. it may be mentioned here that while peaks in the x-ray diffraction pattern characterise crystalline material, peaks in the radial electron density distribution characterise and serve as a "finger print" for amorphous material which lack a long-range order characteristic of crystalline material. The radial distribution specifies the density of atoms or electrons as a function of the radial distance from any reference atom or electron in the system. The peaks in such a distribution correspond to interatomic vectors between atoms present in the material.

For crystalline materials, such information may be readily obtained from the x-ray diffraction pattern by conventional procedures. For amorphous materials, lacking any peaks in the x-ray diffraction pattern, the radial electron density distribution is conventionally utilised to obtain the interatomic vectors. The radial electron density distribution of the material of this invention is illustrated in FIG. 1 of the drawings accompanying this specification wherein MMATS—1 corresponds to an amorphous titanosilicates of composition $TiO_2$:32.5 $SiO_2$. For purpose of comparison the pattern of a sample of crystalline titano-silicates (TS-1) of chemical composition, TiO$_2$:32 SiO$_2$ is also included in FIG. 1. The peaks at 1.6–1.7, 2.7–2.8, 4.1–4.2 and 5.0–5.2 Å correspond to interatomic distance vectors, Si–O$_1$, O$_{1-O2}$, Si$_1$–Si$_2$ (Ti), Si$_1$–O$_2$ (O$_1$–O$_2$) and Si$_1$–Si$_3$(O$_1$–O$_3$), respectively.

Figure 2:
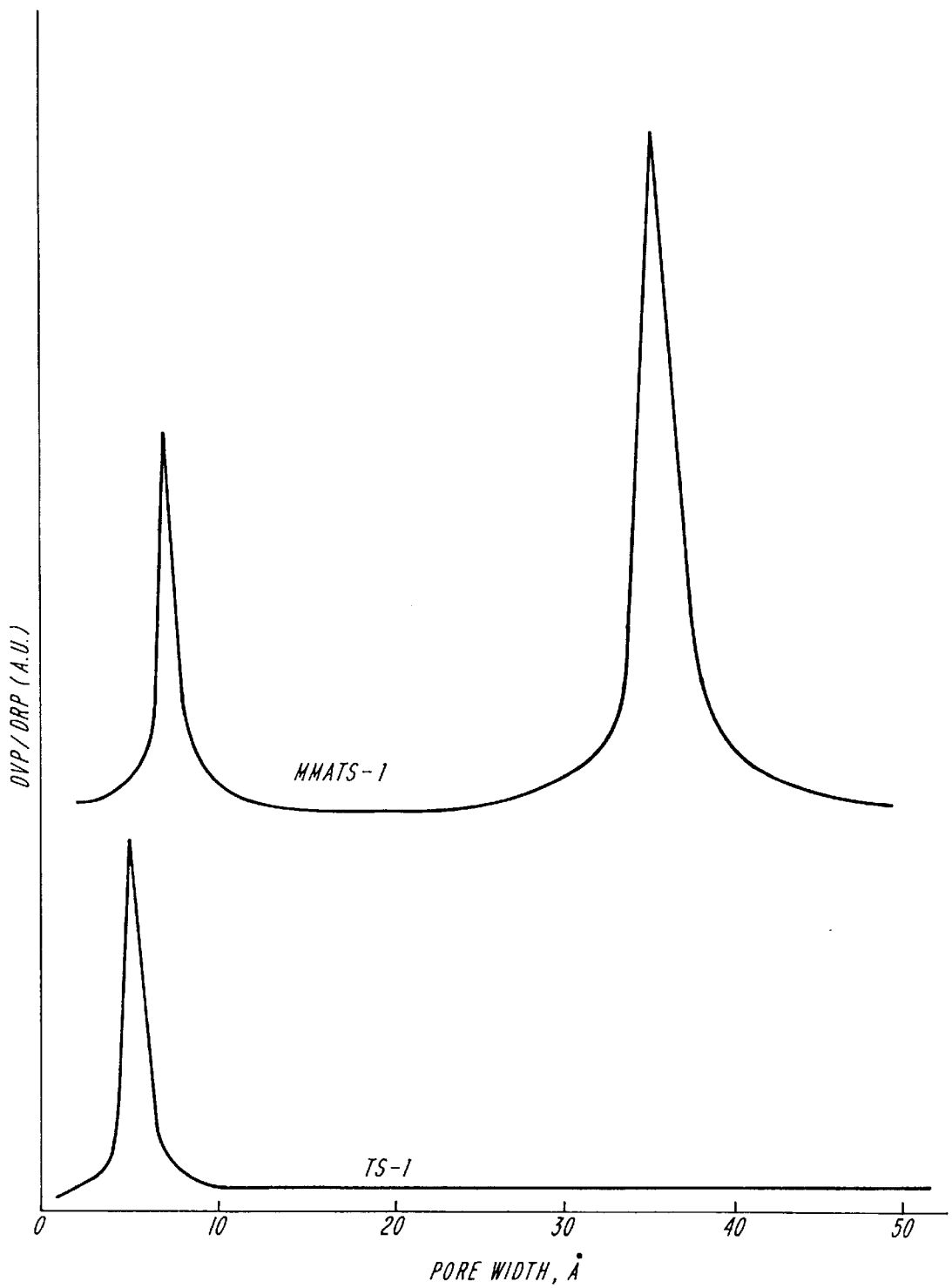
FIG. 2 illustrates a comparison of the pore size distribution of hitherto known crystalline titanosilicate and that of the MMATS sample prepared according to the process of the present invention.

FIG. 2 of the drawings accompanying this specification compares the pore size distribution of the hitherto known crystalline titanosilicate (TS-1) and that of the MMATS (with Si/Ti=34) sample prepared according to the process of the present invention. This is obtained by the nitrogen adsorption-desorption method by using omnisorp 100 CX (Omicron, USA) apparatus. The surprising and illuminating information from FIG. 2 of the drawings accompanying this specification is that even though the MMATS material is (1) amorphous, (2) possess a bimodal pore size distribution including meso pores in the range 10–100Å and (3) were synthesised at a pH=7 in the absence of any nitrogenated organic base at low temperatures and atmospheric pressure.

The immediate environment of Si and Ti atoms in MMATS, as revealed by the position of the interatomic vectors, which is represented in FIGS. 1 and 2 of the drawings accompanying this specification, is surprisingly similar to that prevailing in TS-1 which is (1) crystalline with a well defined x-ray diffraction pattern, (2) possesses a single value of the pore width of around 5.5 Å and no pores with width in the meso pore range above 10 Å and (3) which can be synthesised only at a pH above 10 in the presence of a nitrogenated organic base as described in U.S. Pat. No. 4,410,501.

The preferred oxidising agent used in the process of this invention is hydrogen peroxide, especially in aqueous solutions. The concentration of H$_2$O$_2$ in the aqueous solution may vary from 5 to 30 wt. %. As to the relative amount of hydrogen peroxide and hydrocarbon compound to be used in the process of the present invention, it has been observed that a high efficiency of peroxide utilisation can be achieved using molar ratios of hydrocarbon to hydrogen peroxide in the range 1 to 5.

In one variant of the process, solvents can be used to increase miscibility and to provide at least micro homogeneity of the aqueous H$_2$O$_2$ solution and the hydrocarbon compound with consequent beneficial effects. The purpose of the solvent is to solubilise, at least in part, both the hydrocarbon compound and H$_2$O$_2$, and, so long as the solvent accomplishes this without significantly decreasing the utilisation efficiency of H$_2$O$_2$ and without being itself involved in chemical reaction, its nature Is unimportant. Thus, methanol, acetone, tertiary butanol and acetonitrile have been used with advantage in our invention.

In another embodiment of the present invention, the process described hereinafter may be practised either in a batch or in a continuous mode. In the case of a batch-mode of operation, the catalyst, in the form of spherical granules or powder, is used in an amount from about 5 upto perhaps 50 wt % based on the hydrocarbon substrate to be oxidised. Reaction times of 24 hours generally suffice. Reaction temperatures may be between 10° to 90° C. and preferably at as low a temperature within this range as is consistent with an acceptable reaction rate.

The process described in the present invention may also be practised in the continuous mode reactor either of the fixed or fluidised bed type of reactor containing the amorphous titanium-silicate catalyst possessing all the six distinctive features mentioned hereinbefore. The use of a homogeneous feedstock is advantageous in ensuring adequate contact between H$_2$O$_2$, the hydrocarbon and the catalyst.

The process for the preparation of amorphous titanium-silicate catalysts (MMATS) of the characteristics hereinabove mentioned has been described in our copending Indian application No. 1508/DEL/94. In brief, the process comprises of reacting an alkoxide of titanium with an alkoxide of silicon in the presence of water at a temperature in the range of 20° to 90° C., drying the resultant precipitated amorphous titanium-silicate in the range of 100° to 150° C. and further calcining the dried powder at a temperature above 400° C. Alkoxides which may be advantageously used include ethoxides, isopropoxides and butoxides. It has been observed during the course of the investigations leading to the present invention that as long as the amorphous titanium-silicate possesses the six distinctive features mentioned hereinbefore, it can be used advantageously as a catalyst in the oxidation process.

A significant feature in the preparation of the catalysts used in the process of the present invention is that nitrogenated organic bases, like tetramethyl ammonium hydroxides, tetraethyl ammonium hydroxide, tetrapropyl ammonium hydroxide or tetrabutyl ammonium hydroxide are to be avoided in the synthesis mixture of the catalyst preparation as their presence leads to the formation of crystalline phases like TS-1, which are not suitable for oxidation of bulky hydrocarbons like naphthalene or anthracene.

While the region of the unique activity of the amorphous titanium-silicates with the six distinctive features mentioned hereinabove in the hydrocarbon oxidation is not clear, it may be speculated that the presence of isolated tetravalent titanium ions in tetrahedral coordination positions as indicated by the absorption band at 220 nm may cause the selective oxidation of the hydrocarbons. B. Notari in "Innovation in Zeolite materials Science" (Studies in Surface Science and Catalysis, Vol. 37, P. J. Grobet et al. editors, pub. Elsevier, Amsterdam, 1988, p. 413) had postulated that isolated Ti$^{4+}$ ions in tetrahedral crystalline framework structure are the active sites in the TS-1 catalysts. It is possible that the amorphous titanium-silicate catalysts used in the process of the present invention contain a majority of the Ti atoms as isolated Ti$^{4+}$ ions in tetrahedral coordination but in an amorphous silicate matrix thereby leading to their distinctive ability to oxidise bulkier hydrocarbons. A crystalline matrix with a narrow uniform pore dimension like TS-1 would not be suitable in the present process.

The process of the present invention is described hereinbelow with the following examples which are only illustrative and need not be construed to limit the scope of the present invention in any manner whatsoever.

EXAMPLE 1

Preparation of the Amorphous Titanium-Silicate Catalyst 1 mole of tetraethyl orthosilicate was slowly added to 0.1 mole of titanium butoxide at 40° C. and neutral pH over a period of 6 hours. Water was then added in a controlled manner to the above mixture in such a way that a clear transparent gel was obtained. The material was aged at 40° C. for 24 hours after which the H$_2$O and alcohol were removed by vacuum treatment. The resultant semi-dry gel was dried in an oven at 110° C. for 24 hours and further calcined at 400° C. for 24 hours. The final titanium-silicate had a chemical composition in terms of the mole ratios of the anhydrous oxides as TiO$_2$:10 SiO$_2$. It was completely amorphous as indicated by the absence of any peaks in the x-ray diffraction pattern. The average pore radius was 8 Å and meso-pore radius of 18 Å. The material exhibited an absorption band at 225 nm in the ultraviolet and another band at 960 cm$^{-1}$ in the infrared region of the absorption spectrum.

The MMATS also exhibited interatomic vectors in the radial electron density distribution at 1.62, 2.75, 3.23, 4.18 and 5.11 Å, respectively. Following the same procedure, but varying the molar ratios of tetraethyl orthosilicate and titanium butoxide titanium-silicates with Si/Ti molar ratios of 85, 162 and 350 were prepared. All of them were amorphous and exhibited the absorption bands around 220 nm and 960 cm$^{-1}$;

Values of pore mexima and interatomic vectors were also similar.

EXAMPLES 2 TO 12

An amorphous titanium-silicate with a Si/Ti molar ratio of 10 and prepared as described in Example 1 was utilised in all the catalytic runs. The experiments were conducted in a round-bottomed flask immersed in an oil bath and fitted with a water condenser. The reactant hydrocarbon (0.1 m mole) in a suitable solvent such as methanol, t-butanol, acetone or water etc. depending upon the nature of the Input hydrocarbon or it's derivative was taken in the round bottomed flask and equilibrated at the reaction temperature for 30 min. A quantity of catalyst powder equal to 10% by wt. of the hydrocarbon was next added. An aqueous solution of 30% $H_2O_2$ (0.04 m mole) was then added slowly over a period of 6 hours and the reaction continued for another 18 hours. At the end of a total of 24 hours reaction period, the contents of the flask were cooled. The catalyst was removed by filtration. A sample of the filtrate (one microliter) was analysed by capillary gas chromatography (Hewlett Packard 5880). The hydrocarbons or their derivatives used in the experimental runs, the major products formed, the reaction conditions, the solvent used, the percent selectivity to the major product formed and the overall conversion observed in mole percent, are given in Table 3. A comparison of activity of the present catalyst with that of the crystalline titanosilicate (TS1) is given in Table 2 while Table 1 indicates the feasibility of carrying out hydroxylation of some organic substrate in TS1 and the present catalyst, MMATS (as indicated by 'yes' or 'no').

TABLE 3

Oxidation of hydrocarbons or their derivatives

| Ex. No. | Reactant | Major product | Temp. (°C.) | Solvent | Major product sel. % | Conversion mol. % |
|---|---|---|---|---|---|---|
| 2 | Benzene | Phenol | 50 | t-Butanol | 81 | 52 |
| 3 | Toluene | Cresol | 80 | t-Butanol | 85 | 58 |
| 4 | Napthalene | Napthol | 80 | Acetone | 75 | 68 |
| 5 | n-Hexane | n-Hexanol | 50 | Acetone | 71 | 62 |
| 6 | Cyclohexane | Cyclohexanol | 52 | Acetone | 86 | 68 |
| 7 | 2-Napthol | 2,6-Napthol | 85 | Acetone | 63 | 45 |
| 8. | Propylene | Propylene Oxide | 45 | Methanol | 96 | 90 |
| 9. | Allyl Alcohol | Glycidol | 50 | Water | 75 | 82 |
| 10 | Phenol | Catechol/hydroquinone | 80 | Water | 95 | 90 |
| 11 | Allyl chloride | Epoxide | 45 | Acetone | 85 | 82 |
| 12 | Anthracene | Anthraquinol | 80 | t-Butanol | 76 | 70 |

We claim:

1. A process for the oxidation of hydrocarbons having a general formula RX, wherein R is from n-alkyl selected from the group consisting of methyl, ethyl, propyl, butyl and hexyl, isopropyl, benzyl, cyclohexyl, mono-, di- or tricyclic aryl selected from the group consisting of benzene, napthalene and anthracene or alkenic groups and X is selected from the group consisting of H, OH and Cl to compounds having formula R-HXY wherein wherein R is from n-alkyl selected from the group consisting of methyl, ethyl, propyl, butyl and hexyl, isopropyl, benzyl, cyclohexyl, mono-, di- or tricyclic aryl selected from the group consisting of benzene, napthalene and anthracene or alkenic groups, X has the meaning defined as above and Y=OH; which comprises of reacting the appropriate hydrocarbon of the formula RX where R and X having the meaning defined above, with a solution of aqueous hydrogen peroxide at a temperature in the range of 10°–100° C. in the presence of an amorphous titanium-silicate catalyst having molar chemical composition in terms of the anhydrous oxides of $TiO_2$: (5-400) $SiO_2$ and being further characterised by (a) absence of any line in the x-ray diffraction pattern, (b) presence of a sharp absorption band around 960 cm$^{-1}$ in the infrared region of the absorption spectrum, (c) having an average micropore radius below 10 Å and meso-porous radius below 40 Å, (d) presence of a sharp absorption band around 200 nanometers in the ultraviolet region of the spectrum and (e) presence of interatomic vectors around 1.6–1.7, 2.7–2.8, 4.1–4.2 and 5.0–5.2 Å in the radial electron density distribution; and isolating the resultant products of the oxidation reaction by conventional methods.

2. A process as claimed in claim 1 wherein the concentration of hydrogen peroxide in the aqueous solution varies from 5 to 30 wt %.

3. A process as claimed in claim 1 wherein the molar ratio of hydrocarbon to hydrogen peroxide is in the range of 1 to 5.

4. A process as claimed in claim 1 wherein solvents are added to the reaction to increase miscibility and to provide at least micro homogeneity of the aqueous solution and the hydrocarbon compounds.

5. A process as claimed in claim 1 wherein the reaction is conducted in one of a batch mode and a continuous mode, and in the case of a batch-mode of operation, the catalyst is in the form of spherical granules or powder which is in an amount from about 5 to 50 wt % based on the hydrocarbon substrate to be oxidised.

6. A process as claimed in claim 1 wherein the reaction time is about 24 hrs.

7. A process as claimed in claim 1 wherein the oxidised hydrocarbon is recovered by distillation, condensation or solvent extraction.

8. The process of claim 1, wherein the solution of aqueous hydrogen peroxide is at a temperature between 50° and 100° C.

* * * * *

UNITED STATES PATENT AND TRADEMARK OFFICE
CERTIFICATE OF CORRECTION

PATENT NO.    : 5,811,599
DATED         : September 22, 1998
INVENTOR(S)   : Keshavaraja Alive et al.

It is certified that error appears in the above-identified patent and that said Letters Patent is hereby corrected as shown below:

<u>Title page,</u>
Insert the following Assignee information: -- [73] Assignee: Council of Scientific and Industrial Research, New Delhi (IN) --

Signed and Sealed this

Eighth Day of July, 2003

JAMES E. ROGAN
*Director of the United States Patent and Trademark Office*